United States Patent [19]

Felman et al.

[11] Patent Number: 5,438,056
[45] Date of Patent: Aug. 1, 1995

[54] HETEROCYCLIC OXIME CARBAMATES

[75] Inventors: Steven W. Felman, Granger, Ind.; Kevin A. Memoli, Cranbury; Ivo Jirkovsky, Plainsboro, both of N.J.

[73] Assignee: American Home Products Corporation, Madison, N.J.

[21] Appl. No.: 131,820

[22] Filed: Oct. 5, 1993

[51] Int. Cl.$^6$ .................. A61K 31/54; C07D 311/80; C07D 221/16

[52] U.S. Cl. ................. 514/224.5; 514/320; 514/324; 514/437; 514/438; 514/454; 514/471; 514/646; 514/649; 514/658; 546/111; 546/238; 549/27; 549/76; 549/390; 549/479; 564/316; 564/336

[58] Field of Search ............ 549/76, 479, 27, 390; 514/437, 438, 454, 471, 320, 324, 224.5, 649, 646, 658; 546/111, 238; 564/316, 336

[56] References Cited

U.S. PATENT DOCUMENTS 3,290,320 12/1966 Villani .......................... 260/295

FOREIGN PATENT DOCUMENTS 1070964 6/1967 United Kingdom .

OTHER PUBLICATIONS

Villani et al J. Pharm. Sci., 58, 138 (1969).

*Primary Examiner*—C. Warren Ivy
*Assistant Examiner*—Amelia Owens
*Attorney, Agent, or Firm*—R. F. Boswell; Walter P. Patton

[57] ABSTRACT

The compounds of the present invention have the following formula:

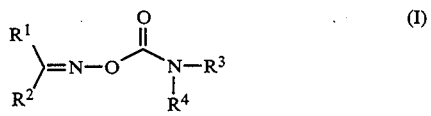

(I)

wherein $R^1$ and $R^2$ are independently phenyl, pyridyl, thienyl, naphthyl, substituted phenyl wherein the substituent is selected from the group consisting of halogen, methoxy, and dialkylamino wherein alkyl contains 1 to 3 carbon atoms; or $R^1$ and $R^2$ are independently substituted furanone of the structure

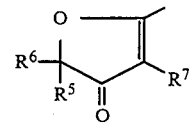

wherein $R^5$ and $R^6$ are independently alkyl containing 1 to 3 carbon atoms, cycloalkyl containing 5 to 7 carbon atoms, phenyl or substituted phenyl wherein the substituent is alkyl containing 1 to 5 carbon atoms or halogen; $R^7$ is hydrogen or halogen; or $R^1$ and $R^2$ are joined to form

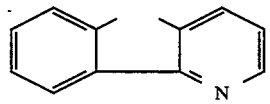

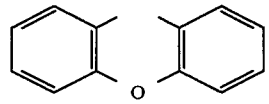

or

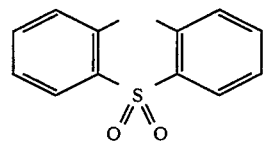

$R^3$ and $R^4$ are independently hydrogen, alkyl containing 4 to 20 branched, straight chain, cyclic, saturated or unsaturated carbon atoms; or $R^3$ and $R^4$ are joined to form (Abstract continued on next page.)

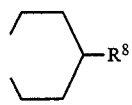
wherein $R^8$ is alkyl containing 1 to 3 carbon atoms which possess blood-glucose lowering activity, to processes for preparation thereof, pharmaceutical compositions comprising the same, and to the method of using the same in the reduction of excess cholesterol in human beings and animals.
6 Claims, No Drawings

HETEROCYCLIC OXIME CARBAMATES

SUMMARY OF INVENTION

The present invention relates to novel heterocyclic oxime carbamates which inhibit cholesterol absorption, to processes for their production, pharmaceutical compositions containing them, and to methods for their use.

PRIOR ART

The lower alkyl benzoyl-pyridine oxime carbamates have been disclosed by Villani in U.S. Pat. No. 3,290,320 and Great Britain Patent No. 1,070,964 and in Villani et al J. Pharm. Sci., 58, 138 (1969).

The compounds of the present invention have the following formula:

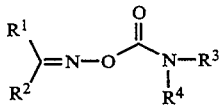
(I)

wherein $R^1$ and $R^2$ are independently phenyl, pyridyl, thienyl, naphthyl, substituted phenyl wherein the substituent is selected from the group consisting of halogen, methoxy, and dialkylamino wherein alkyl contains 1 to 3 carbon atoms; or $R^1$ and $R^2$ are independently substituted furanone of the structure

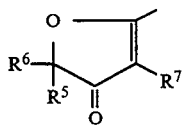

wherein $R^5$ and $R^6$ are independently alkyl containing 1 to 3 carbon atoms, cycloalkyl containing 5 to 7 carbon atoms, phenyl or substituted phenyl wherein the substituent is alkyl containing 1 to 5 carbon atoms or halogen; $R^7$ is hydrogen or halogen; or
$R^1$ and $R^2$ are joined to form

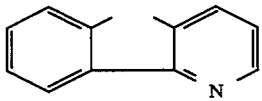

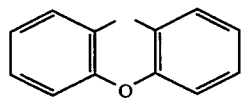

or

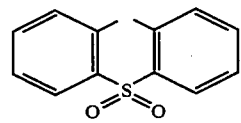

$R^3$ and $R^4$ are independently hydrogen, alkyl containing 4 to 20 branched, straight chain, cyclic, saturated or unsaturated carbon atoms; or
$R^3$ and $R^4$ are joined to form

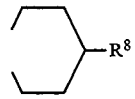

wherein $R^8$ is alkyl containing 1 to 3 carbon atoms.

The preferred compounds of the present invention have formula (II)

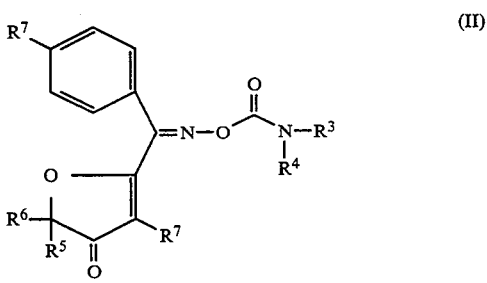
(II)

wherein $R^5$ and $R^6$ are independently alkyl containing 1 to 3 carbon atoms, cycloalkyl containing 5 to 7 carbon atoms, phenyl or substituted phenyl wherein the substituent is alkyl containing 1 to 5 carbon atoms or halogen; $R^7$ is hydrogen or halogen;
$R^3$ and $R^4$ are independently alkyl containing 4 to 20 branched, straight chain, cyclic, saturated or unsaturated carbon atoms.

The further preferred compounds of the present invention are described by the following examples:

1. 2,2-Dimethyl-5-[[[[(octylamino)carbonyl]oxy]imino]phenylmethyl]-3(2H)-furanone
2. 2,2-Dimethyl-5-[[[[(dodecylamino)carbonyl]oxy]imino]phenylmethyl]-3(2H)-furanone
3. 2,2-Dimethyl-5-[[[[(4,4dimethylcyclohexyl)amino]carbonyl]oxy]imino]phenylmethyl]-3(2H)-furanone
4. 2,2-Dimethyl-5-[[[[(2)-9-octadecenylamino]carbonyl]oxy]imino]phenylmethyl]-3(2H)-furanone
5. 2,2-Dimethyl-5-[[[[(E)-10-nonadecenylamino]carbonyl]oxy]imino]phenylmethyl]-3(2H)-furanone
6. 2,2-Dimethyl-5-[[[[(E,E)-9,12-octadecadienylamino]carbonyl]oxy]imino]phenylmethyl]-3(2H)-furanone
7. 2-Cyclohexyl-2-methyl-5-[[[[(octylamino)carbonyl]oxy]imino]phenylmethyl]-(2H)-furanone
8. 2-Methyl-2-phenyl-5-[[[[(octylamino)carbonyl]oxy]imino]phenylmethyl]-3(2H)-furanone
9. 2-(4-Chlorophenyl)-2-methyl-5-[[[[(octylamino)carbonyl]oxy]imino]phenylmethyl]-3(2H)-furanone
10. 2-[4-(1,1- Dimethylethyl)phenyl]-2-methyl-5-[[[[(octylamino) carbonyl]oxy]imino]phenylmethyl]-3(2H)-furanone
11. 2,2-Dimethyl-4-bromo-5-[[[[(dodecylamino)carbonyl]imino]phenylmethyl]-3(2H)-furanone
12. 2,2-Dimethyl-5-[(4-chlorophenyl)[[(dodecylamino)carbonyl]imino]methyl]-2(3H)-furanone
13. Phenyl(2-pyridinyl)methanone O-[(cyclohexylamino)carbonyl]oxime
14. Phenyl(2-pyridinyl)methanone O-[(octylamino)carbonyl]oxime
15. Di(2-pyridinyl)methanone O-[(octylamino)carbonyl]oxime 16. (4-Fluorophenyl)(2-pyridinyl)methanone O-[(octylamino)carbonyl]oxime
17. (4-Methoxyphenyl)(2-pyridinyl)methanone O-[(octylamino)carbonyl]oxime
18. (2-Pyridinyl)(2-thienyl)methanone O-[(butylamino)carbonyl]oxime
19. [(Dimethylamino)phenyl](2-pyridinyl)methanone O[(butylamino)carbonyl]oxime
20. (1-Naphthalenyl)(2-pyridinyl)methanone O-[(octylamino)carbonyl]oxime
21. 5H-Indeno[1,2-b]pyridin-5-one O-[(octylamino)carbonyl]oxime
22. 5H-Indeno[1,2-b]pyridine-5-one O-[(4-methyl-1-piperidinyl)carbonyl]oxime
23. 9H-Xanthen-9-one O-[(butylamino)carbonyl]oxime
24. 9H-Thiaxanthen-9-one O-[(butylamino)carbonyl]oxime 10,10-dioxide The present invention also provides pharmaceutical compositions which comprises a compound of this invention and a pharmaceutically acceptable carrier. In particular, the present invention provides pharmaceutical compositions which inhibit cholesterol absorption, which comprises an effective amount of a compound of this invention and a pharmaceutically acceptable carrier.

The compositions are preferably adapted for oral administration. However, they may be adapted for other modes of administration, for example parenteral administration.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like.

The present invention further provides a compound of the invention for use as an active therapeutic substance. Compounds described in this invention are of particular use in inhibiting cholesterol absorption.

The present invention further provides a method of inhibiting cholesterol absorption in mammals including man, which comprises administering to the afflicted mammal an effective amount of a compound or a pharmaceutical composition of the invention.

The compounds of the present invention are prepared by the following Synthetic Schemes:

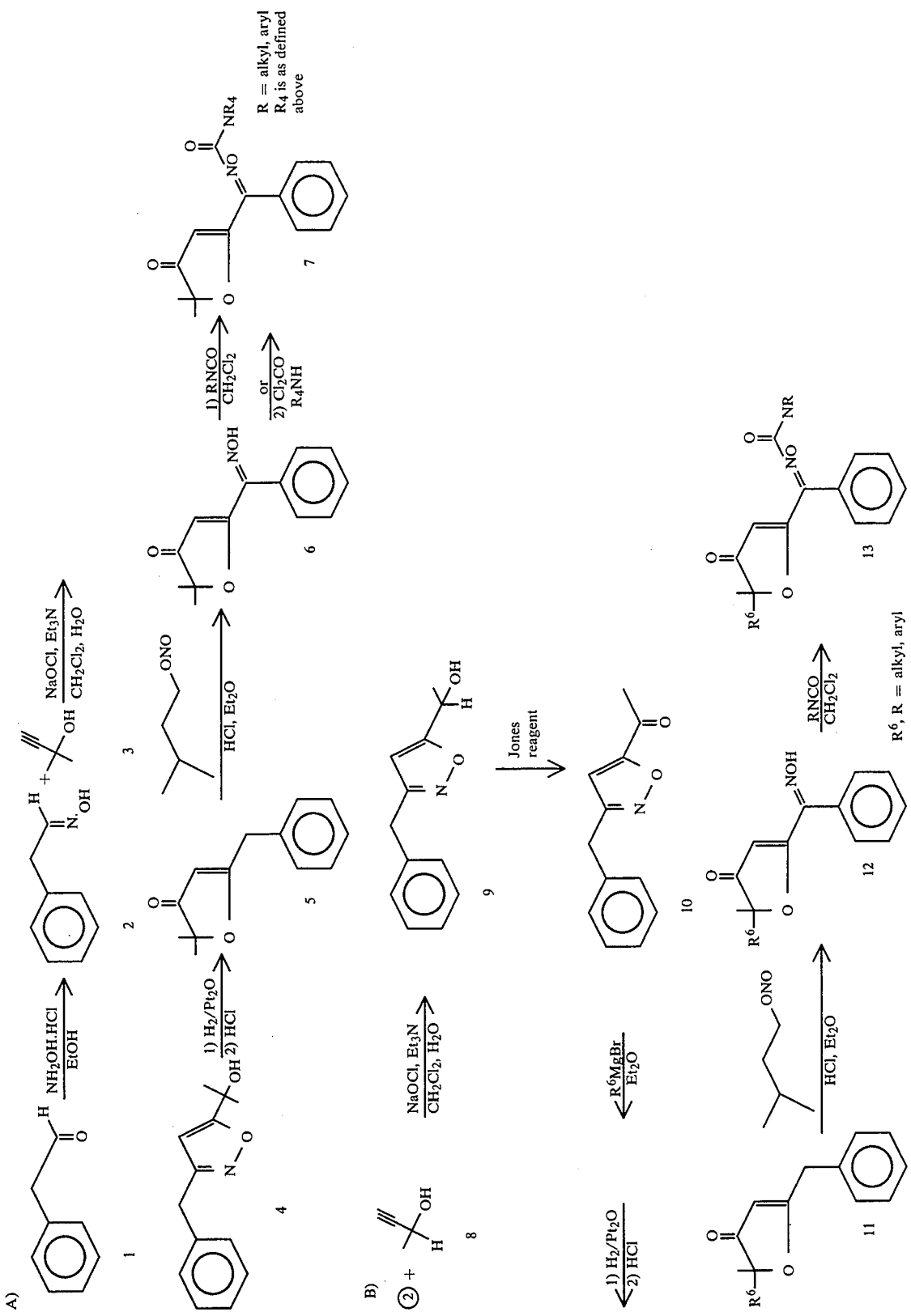

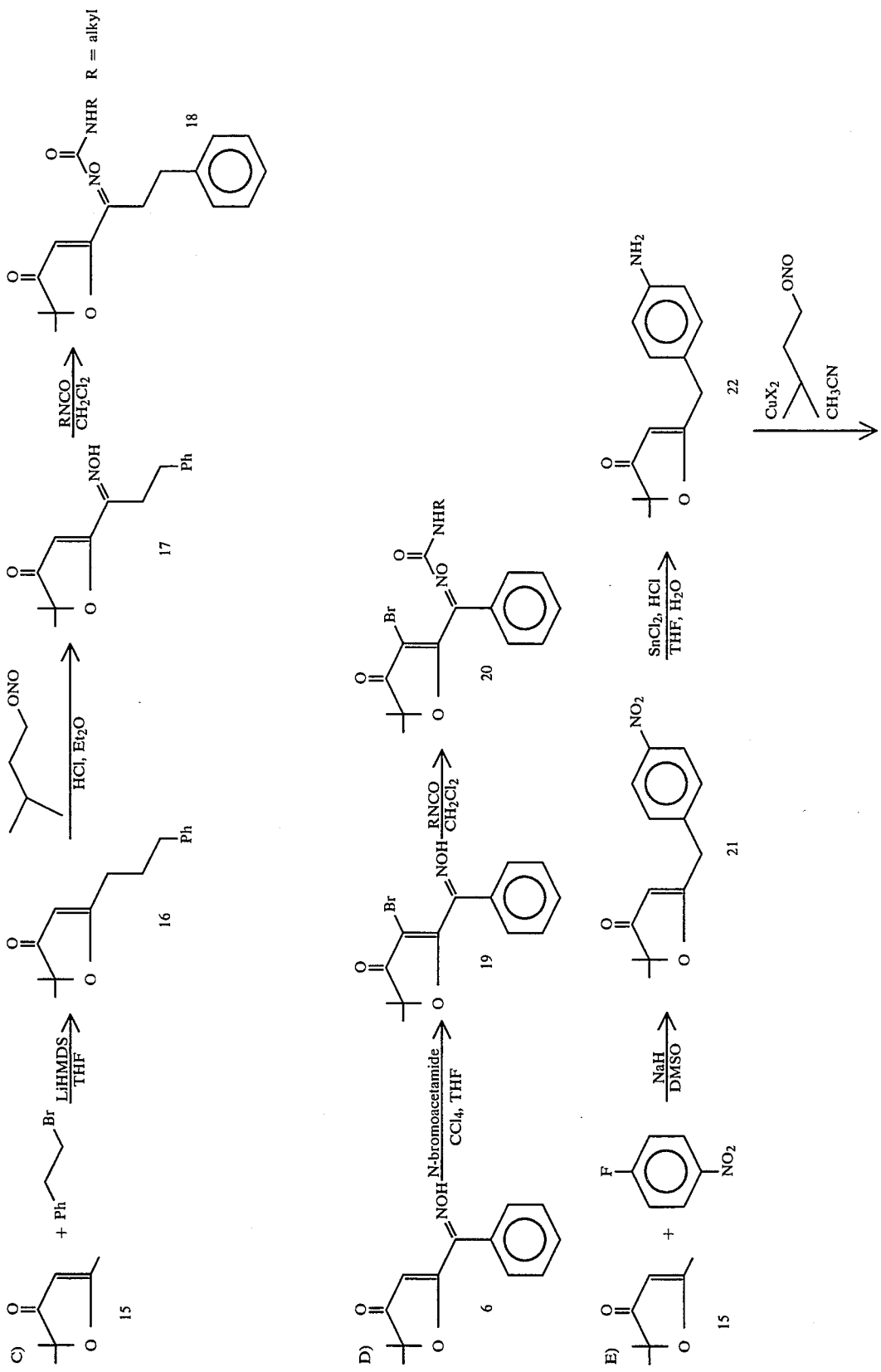

-continued
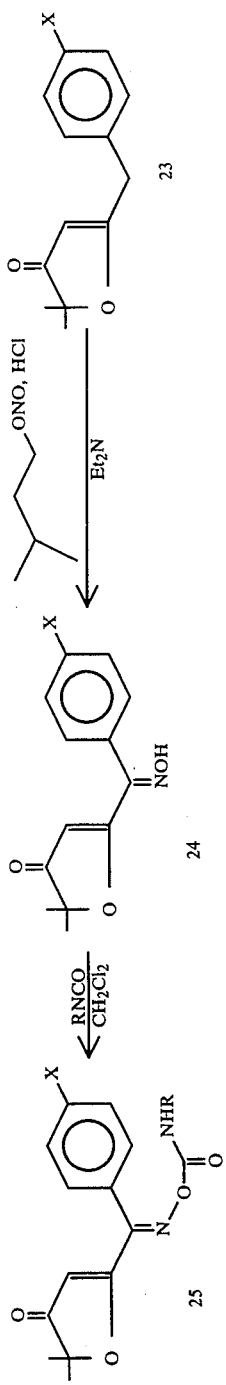
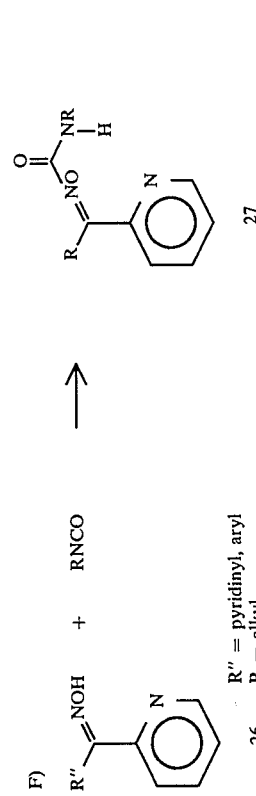
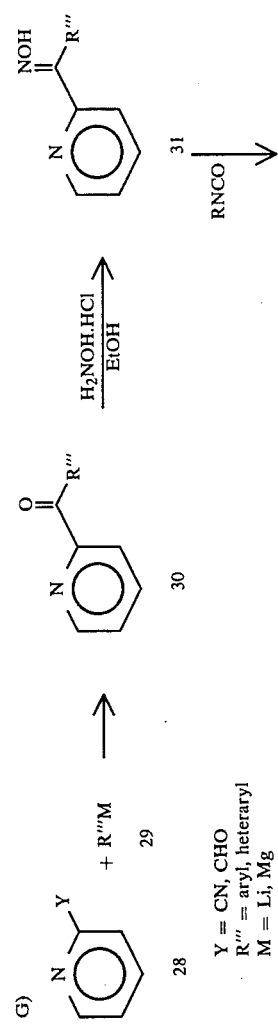
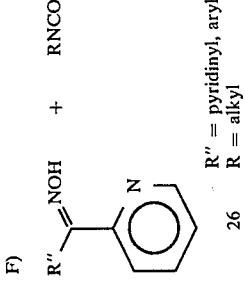
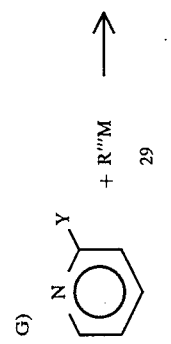

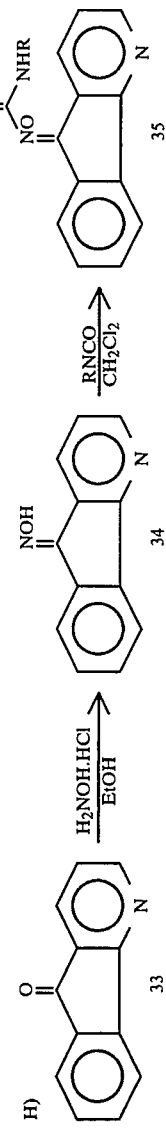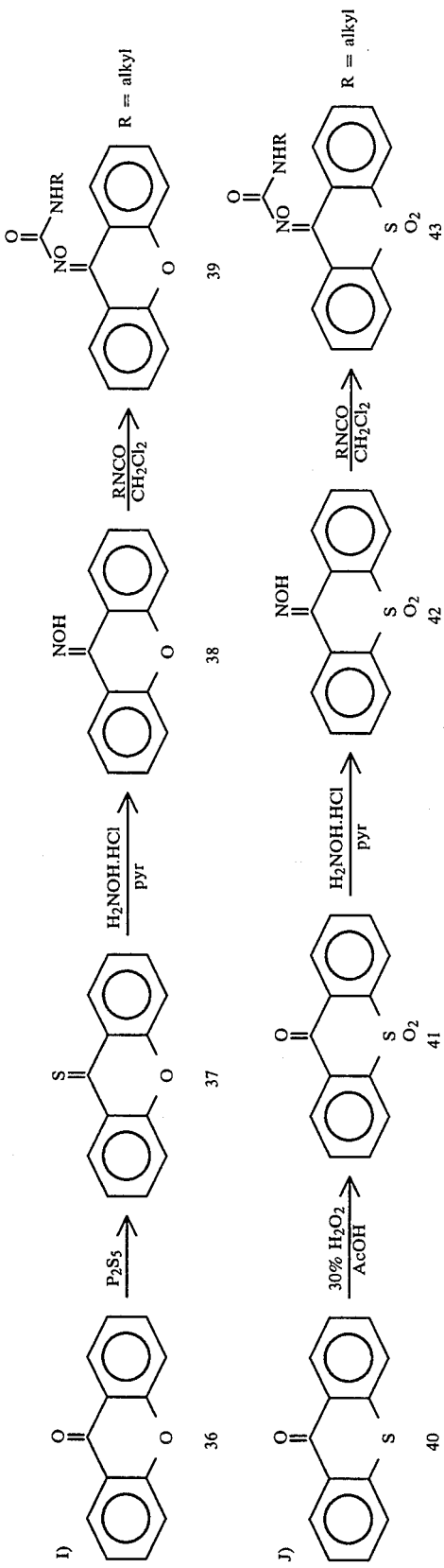

The following Examples further illustrate this invention.

EXAMPLE 1

2,2-Dimethyl-5-[[[[(octylamino)carbonyl]oxy]imino]-phenylmethyl]-3(2H)-furanone

To a solution of phenylacetaldehyde (100 g, 0.83 M) in ethanol (300 mL) at 0° C. was added a solution of hydroxyl amine hydrochloride (63.6 g, 0.91M), 5% aqueous sodium hydroxide (160 g, 0.95M) and water (300 ml). The solution was adjusted to pH12 and was allowed to stir overnight at room temperature. Water (200 ml) was added and the solution was concentrated under vacuum to a constant volume. Ethyl acetate (400 ml) was added, and the layers separated. The organic layer was washed with saturated aqueous sodium chloride (3×100 ml), dried over MgSO$_4$, filtered and concentrated under vacuum to yield a white solid oxime (9.2 g 82% ); m.p. 84°–87° C. $^1$H NMR (CDCl$_3$, 200 MHz) δ3.42 (s, 2H, A isomer), 3.50 (d, J=4 Hz, 2H, B isomer), 4.40 (d, J=4 Hz, 1H), 2.25 (m, 5H), 10.62 (s, 1H, A isomer), 10.91 (s, 1H, B isomer).

To a solution of oxime (11 g, 200 mM), 2-methyl-3-butyn-2-ol (30 g, 350 mM) and triethylamine (6 ml) in chloroform (500 ml) in a one 3-necked round bottom flask fitted with a mechanical stirrer at 0° C. was added bleach (~5% aqueous sodium hypochlorite, 450 ml) dropwise over one hour. The solution was allowed to stir overnight at room temperature. Then the layers were separated. The aqueous layer was extracted with chloroform (2×200 ml). The combined organic layer was washed with saturated aqueous sodium chloride (3×100 ml), dried over MgSO$_4$, filtered and concentrated under vacuum to yield a dark oil (25.6 g, 62%). $^1$H NMR (CDCl$_3$, 200 MHz) δ: 1.55 (s, 6H), 3.96 (s, 2H), 5.9 (s, 1H), 7.25 (m, 5H).

In a 250 ml Parr hydrogenation flask, isoxazole (25.6 g, 110 ml), platinum oxide (1 g) and Raney Ni (1 scoop) were added slowly to a solution of methanol (250 ml) and water (15 ml). The solution was hydrogenated at 50 psi for 24 hours. Then the solution was degassed, and the catalyst was filtered. After the solution was concentrated under vacuum, tetrahydrofuran (300 ml) and 1N aqueous hydrochloric acid (100 ml) were added. The solution was stirred overnight. The tetrahydrofuran was removed under vacuum and ethyl ether (150 ml) was added to the residue. The ethereal layer was washed with saturated aqueous sodium chloride (3×60 ml), dried over MgSO$_4$, filtered and concentrated under reduced pressure to yield a dark oil. The product was purified by column chromatography (silica gel, 9:1, petroleum: ethyl acetate) to yield a clear oil (9.5 g, 43%). $^1$H NMR (CDCl$_3$, 200 MHz): δ1.35 (s, 6H), 3.77 (s, 2H), 7.26 (s, 1H), 7.26 (m, 5H).

To a solution of isoamyl nitrite (15 ml, 112 mM) in 1N ethereal hydrochloric acid (300 ml) at 0° C. was added a solution of furanone (18.8 g, 93 mM) in ether (50 ml) dropwise. The solution was allowed to stir overnight at room temperature. Then the reaction was concentrated under vacuum to a yellow solid. The product was triturated with 4:1 hexane-ethyl acetate overnight, filtered and dried under vacuum to afford light tan solid oxime (16.4 g, 62%); m.p.183°–185° C. $^1$H NMR (CDCl$_3$, 200 MHz): δ1.64 (s, 6H), 5.57 (s, 2H), 7.21 (m, 5H), 12.6 (s, 1H).

To a solution of oxime (4 g, 17.3 mM) in pyridine (6 ml) was added 4-dimethylaminopyridine (DMAP, 10 mg) then octylisocyanate (5.4 g, 34.6 mM). The resulting solution was allowed to stir at room temperature overnight. Ethyl acetate (100 ml) was added and the resulting solution was washed with saturated aqueous sodium bicarbonate (2×50 ml), 1N aqueous hydrochloric acid (2×50 ml) and saturated aqueous sodium chloride (2×50 ml). The organic layer was dried over MgSO$_4$, filtered and concentrated under vacuum to yield a yellow solid. The crude solid was purified by column chromatography (silica gel, methylene chloride-ethyl acetate) and triturated with hexaneoether (9:1) to afford a white solid carbamate (1.8 g, 25%); m.p. 89°–90° C.; MS (EI): 387 (M+H), 83 (100). $^1$H NMR (CDCl$_3$, 400 MHz): 0.88 (t, J=6.8 Hz, 3H), 1.30 (M, 10H), 1.49 (s, 3H), 1.56 (s, 3H), 1.59 (m, 2H), 3.31 (dt, J$_1$6.8 Hz, J$_2$=1.5 Hz, 2H), 6.15 (bs, 1H), 7.45 (m, 5H); Analysis calc'd for C$_{22}$H$_{30}$N$_2$O$_4$: C, 68.37; H, 7.82%; Found: C, 67.99; H, 7.92%.

Example 2 was prepared by the carbamate procedure described in Example 1 except using dodecyl isocyanate.

EXAMPLE 2

2,2-Dimethyl-5-[[[[(dodecylamino)carbonyl]oxy]imino]phenylmethyl]-3(2H)-furanone Prepared in 81% yield; m.p. 83°–84.5° C. $^1$H NMR (CDCl$_3$, 400 MHz): δ0.88 (t, J=6.8 Hz, 3H), 1.26 (m, 18H), 1.48 (s, 6H), 1.59 (m, 2H), 3.31 (dt, J$_1$=6.8 Hz, J$_2$=1.5 Hz, 2H), 6.81 (bs, 1H), 7.45 (m, 5H); Analysis calc'd: C$_{26}$H$_{38}$N$_2$O$_4$: C, 70.56; H, 8.65%; Found: C, 70.49; H, 8.83%.

EXAMPLE 3

2,2-Dimethyl-5-[[[[[(4,4dimethylcyclohexyl)amino]carbonyl]oxy]imino]phenylmethyl]-3(2H)-furanone To a 2M solution of phosgene in toluene (8.8 ml, 17.2 mM) at 0° C. was added a solution of previous oxime (3 g, 13 mM) and N-dimethylaniline (1.23 g, 14.3 mM) in tetrahydrofuran (75 ml) dropwise via syringe pump. The solution was allowed to stir at room temperature overnight. Again the reaction was cooled to 0° C. and a solution of 4,4-dimethylcyclohexylamine (3.3 g, 26 mM) in pyridine (4.1 g, 56 mM) was added dropwise via syringe pump. Again the reaction was allowed to stir at room temperature overnight. Saturated aqueous sodium bicarbonate (100 ml) was added and the solution was reduced to a constant volume under vacuum. Then ethyl acetate (100 ml) was added, the layers were separated and the organic layer was washed with saturated aqueous sodium chloride (3×30 ml). The resulting solution was dried over MgSO$_4$, filtered and concentrated to a oil. The crude product was purified by column chromatography (silica gel, methylene chloride-ethyl acetate) and triturated with hexane-ether (9:1) to afford a white solid carbamate (1 g, 20%); m.p. 116°–117° C.; $^1$H NMR (CDCl$_3$, 400 MHz): δ0.94 (s, 6H), 1.38 (m, 6H), 1.48 (s, 3H), 1.57 (s, 3H), 1.86 (d, J=12.7 Hz, 2H), 3.59 (m, 1H), 5.95 (d, J=7.4 Hz), 7.46 (m, 5H); Analysis calc'd for C$_{22}$H$_{28}$N$_2$O$_4$: C, 68.73; H, 7.34%; Found: C, 68.56; H, 7.30%.

Examples 4 through 6 were prepared by the procedure described in Example 3 using the appropriate amine.

EXAMPLE 4

2,2-Dimethyl-5-[[[[[(Z)-9-octadecenylamino]carbonyl]oxy]imino]phenylmethyl]-3(2H)-furanone Prepared in 20% yield; m.p. 51°–55° C. $^1$H NMR (CDCl$_3$, 400 MHz): δ0.89 (t, J=6.8 Hz, 3H), 1.27 (m, 25H), 1.46 (s, 3H), 1.58 (s, 3H), 2.02 (m, 4H), 3.31 (dt, J$_1$=6.8 Hz, J$_2$=1.5 Hz, 2H), 5.32 (m, 2H), 6.18 (bs, 1H), 7.45 (m, 5H). Analysis calc'd for C$_{32}$H$_{48}$N$_3$O$_4$: C, 73.24; H, 9.22%; Found: C, 73.36; H, 9.32%.

EXAMPLE 5

2,2-Dimethyl-5-[[[[[(E)-10-nonadecenylamino]carbonyl]oxy]imino]phenylmethyl]-3(2H)-furanone Prepared in 11% yield; m.p. 59°–64° C. $^1$H NMR (CDCl$_3$, 400 MHz): δ0.87 (t, J=6.8 Hz, 3H), 1.29 (m, 26H), 1.48 (s, 6H), 1.56 (m, 1H), 1.99 (m, 2H), 5.33 (dt, J$_1$=6.8 Hz, J$_2$=1.5 Hz, 2H), 5.33 (m, 2H), 6.01 (bs, 1H), 245 (m, 5H); Analysis calc'd for C$_{33}$H$_{50}$N$_2$O$_4$: C, 73.57; H, 9.35%; Found C, 73.73; H, 9.19%.

EXAMPLE 6

2,2-Dimethyl-5-[[[[[(E,E)-9,12-octadecadienylamino]carbonyl]oxy]imino]phenylmethyl]-3(2H)-furanone Prepared in 27% yield; m.p. 45°–48° C. $^1$H NMR (CDCl$_3$, 400 MHz): δ0.88 (t, J=6.8 Hz, 3H), 1.31 (m, 18H), 1.49 (s, 6H), 1.58 (m, 1H), 1.97 (m, 4H), 2.66 (bs, 2H), 3.31 (dt, J$_1$=6.8 Hz, J$_2$=1.5 Hz, 2H), 5.40 (m, 4H), 6.16 (t, J=5.6 Hz, 1H), 7.46 (m, 5H); Analysis calc'd for C$_{32}$H$_{46}$N$_2$O$_4$: C, 23.53; H, 8.87%; Found: C, 73.45; H, 8.60%.

EXAMPLE 7

2-Cyclohexyl-2-methyl-5-[[[[(octylamino)carbonyl]oxy]imino]phenyl methyl]-3(2H)-furanone To a solution of oxime 2 (85 g, 0.62M), 3-butyn-2-ol (88 g, 1.25M) and triethylamine (100 ml) in a 3L, three neck round bottom flask fitted with a mechanical stirrer at 0° C. was added bleach (5% aqueous NaOCl, 600 ml) dropwise over 1 hr. The reaction was allowed to stir overnight at room temperature. The layers were separated and the aqueous layer was extracted with chloroform (2×200 ml). The combined chloroform extracts were extracted with saturated aqueous sodium chloride (3×200 ml). The resulting solution was dried over MgSO$_4$, filtered and concentrated to dark oil (132 g, ~100%). The resulting alcohol was dissolved in acetone (700 ml) and was cooled to 0° C. Then a solution of chromium trioxide (92 g, 0.93M), concentrated sulfuric acid (500 ml) and water (500 ml) was added dropwise. The reaction was allowed to stir for one hour at room temperature. Saturated aqueous sodium chloride (400 ml) was added. The acetone was removed under vacuum and the resulting aqueous solution was extracted by dichloromethane (3×300 ml). The combined organic layer was washed with 0.5N aqueous solution of sodium sulfite (100 ml) and saturated aqueous sodium chloride (3×100 ml). The resulting solution was dried over MgSO$_4$, filtered and concentrated under vacuum to give a tan oil (45 g, 36%). $^1$H NMR (CDCl$_3$, 200 MHz): δ2.51 (s, 3H), 4.12 (s, 2H), 6.73 (s, 1H), 7.25 (m, 5H).

To a solution of isoxazole (10 g, 49.7 mM) in dry ether (100 ml) at 0° C. was added 2.0M solution of cyclohexylmagnesium bromide in ether (30 ml, 60 mM) dropwise over one hour. Then, the reaction was allowed to stir for one hour at room temperature. A pH 7 phosphate buffer (100 ml) was added and the suspension was filtered through celite. The celite was washed with ether (100 ml). The combined ethereal layer was extracted with saturated aqueous sodium chloride (3×50 ml), dried over MgSO$_4$, filtered, and concentrated under vacuum to yield a clear oil (11.1 g, 78%).

In a 250 ml Parr hydrogenation flask, platinum oxide (0.3 g), the above isoxazole (11.1 g, 39 mM) and Raney Ni (one scoop) were added slowly to a solution of methanol (100 ml) and water (10 ml). The solution was hydrogenated at 50 psi for 24 hours. The solution was degassed and the catalyst filtered. After the solution was concentrated under vacuum, tetrahydrofuran (75 ml) and 1N aqueous hydrochloric acid (25 ml) were added. The solution was stirred overnight. The tetrahydrofuran was removed under vacuum and ether (100 ml) was added. The ethereal layer was washed saturated aqueous sodium chloride (3×30 ml), dried over MgSO$_4$, filtered and concentrated under vacuum to yield a dark oil. The crude product was purified by column chromatography (silica gel, petroleum ether-ethyl acetate 9:1) to afford a clear oil (3.8 g, 36%). $^1$H NMR (CDCl$_3$, 200 MHz): δ1.12 (m, 4H), 1.30 (s, 3H), 1.62 (m, 7H), 3.75 (s, 2H), 5.21 (s, 1H), 7.24 (m, 5H).

Through a solution of furanone (3.8 g, 14 mM) in ether (75 ml) was bubbled hydrogen chloride gas till a precipitate formed. Then isoamyl nitrite (4 ml, 30 mM) was added dropwise. After the reaction was stirred one hour, saturated aqueous sodium chloride (50 ml) was added. The layers were separated and the organic layer was extracted with saturated aqueous sodium chloride (3×50 ml). The resulting solution was dried over MgSO$_4$, filtered and concentrated to a semicrystalline oil. The crude product was triturated with hexane-ether (9:1) and filtered to afford an off white solid oxime (3.3 g, 78%). $^1$H NMR (DMSO-d$_6$, 200 MHz): δ1.05 (m, 4H), 1.21 (s, 3H), 1.71 (m, 7H), 3.23 (s, 2H), 5.55 (s, 1H), 7.32 (m, 5H), 12.5 (s, 1H).

To a solution of oxime (3.3 g, 11 mM) and DMAP (10 mg) in pyridine (6 ml) was added octylisocyanate (5.4 ml, 33 mM) dropwise. After the reaction was stirred overnight, ethyl acetate (100 ml) was added. The resulting solution was washed with saturated aqueous sodium bicarbonate (2×50 ml), 1N aqueous hydrochloric acid (2×50 ml) and saturated aqueous sodium chloride (2×50 ml). The resulting organic layer was dried over MgSO$_4$, filtered and concentrated to yield a yellow oil. The crude product was purified by column chromatography (silica gel, dichloromethane-ethyl acetate) then recrystallize the solid from hexane-ether (9:1) to afford a white solid (1.85 g, 37%); m.p. 85°–87° C. $^1$H NMR (CDCl$_3$, 400 MHz): δ0.89 (t, J=6.8 Hz, 3H), 1.21 (m, 16H), 1.42 (s, 3H), 1.60 (m, 5H), 1.76 (m, 2H), 1.91 (d, J=11.5 Hz 1H), 3.34 (dt, J$_1$=6.8 Hz, J$_2$=1.5 Hz, 2H), 5.74 (s, 1H), 6.23 (t, J$_1$=5.8 Hz, 1H), 7.45 (m, 5H); Analysis calc'd for C$_{27}$H$_{38}$N$_2$O$_4$: C, 71.34; H, 8.43%; Found C, 71.33; H, 8.54%.

The compounds of Examples 8 through 10 were prepared by the procedure described in Example 7 using the appropriate Grignard reagent.

EXAMPLE 8

2-Methyl-2-phenyl-5-[[[[(octylamino)carbonyl]oxy]imino]phenylmethyl]-2(3H)-furanone Prepared in 52% yield: m.p. 74°–76° C. $^1$H NMR (CDCl$_3$, 400 MHz): δ0.87 (t, J=6.8 Hz, 3H), 1.30 (m, 8H), 1.61 (t, J=6.8 Hz, 2H), 1.84 (s, 3H), 3.31 (dt, $J_1$=6.8 Hz, $J_2$=5.5 Hz, 2H), 5.73 (s, 1H), 6.27 (t, J=5.5 Hz, 1H), 7.43 (m, 5H); MS (FAB): 449 (M+H), 145 (100); Analysis calc'd for $C_{27}H_{32}N_2O_4$: C, 72.30; H, 7.19%; Found: C, 71.92; H, 7.06%.

EXAMPLE 9

2-(4-Chlorophenyl)-2-methyl-5-[[[[(octylamino)carbonyl]oxy]imino]phenylmethyl]-3(2H)-furanone Prepared in 74% yield; m.p. 89°–91° C. $^1$H NMR (CDCl$_3$, 400 MHz): δ0.87 (t, J=6.4 Hz, 3H), 1.29 (m, 8H), 1.60 (t, J=6.8 Hz, 2H), 3.33 (dt, $J_1$=6.8 Hz, $J_2$=5.5 Hz, 2H), 5.74 (s, 1H), 6.18 (t, J=5.5 Hz, 2H), 7.43 (m, 5H); MS (FAB): 483 (M+H), 179 (100); Analysis calc'd for $C_{27}H_{31}N_2O_4Cl$: C, 67.14; H, 6.47%; Found C, 67.07; H, 6.62%.

EXAMPLE 10

2-[4-(1,1-Dimethylethyl)phenyl]-2-methyl-5-[[[[(octylamino)carbonyl]oxy]imino]phenylmethyl]-3(2H)-furanone Prepared in 62.5% yield; m.p. 74°–76° C. $^1$H NMR (CDCl$_3$, 400 MHz): δ0.87 (t, J=6.6 Hz, 3H), 1.28 (m, 8H), 1.30 (s, 18H), 1.60 (t, J=6.6 Hz, 2H), 3.33 (dt, $J_1$=6.8 Hz, $J_2$=5.5 Hz, 2H), 5.71 (s, 1H), 6.30 (t, J=5.6 Hz 1H), 7.43 (m, 5H); MS (FAB): 504 (M+H), 57 (100); Analysis calc'd for $C_{31}H_{40}N_2O_4$: C, 73.14; H, 5.18%; Found: C, 73.36; H, 7.94%.

EXAMPLE 11

2,2-Dimethyl-5-[1-[[[(octylamino)carbonyl]oxy]imino]2-phenylethyl]-3(2H)-furanone To a solution of 3,5,5-trimethyl-3(2H)-furanone (2.0 g, 15.8 mM) in dry tetrahydrofuran (40 mL) at −78° C. was added a 1.0M solution of lithium bis(trimethylsilyl)amide in tetrahydrofuran (17.5 mL, 17.5 mM). The resulting solution was stirred for 20 minutes. Then phenethyl bromide (10.8 mL), 39.7) was added dropwise. The reaction was allowed to warm to room temperature and stir overnight. The reaction was diluted with saturated aqueous sodium chloride (150 mL). The resulting mixture was extracted with ether (3×100 mL). The combined ethereal extracts were dried over MgSO$_4$, filtered and concentrated under vacuum to yield a yellow liquid (13.3 g). The crude product was purified by column chromatography (silica gel, dichloromethane-ethyl acetate) to yield a colorless oil (800 mg, 22%). $^1$H NMR (CDCl$_3$, 200 MHz): δ1.30 (s, 6H), 1.97 (m, 2H), 2.41 (t, J=8 Hz, 2H), 2.62 (t, J=8 Hz 2H), 5.28 (s, 1H), a7.15 (m, 5H).

To 1N ethereal hydrochloric acid solution (10 mL) was added ketone (1.16 g, 5 mM) then isoamyl nitrite (669 mg, 5.5 mM). The reaction was allowed to stir overnight at room temperature. Then, the solvent was removed under vacuum and the yellow residue was triturated with petroleum ether (10 mL). The mixture was filtered and washed with petroleum ether to afford a white solid oxime. (910 mg, 70% ). $^1$H NMR (CDCl$_3$, 200 MHz): δ1.38 (s, 6H), 2.94 (t, J=8 Hz, 2H), 3.05 (t, J =8 Hz, 2H), 5.83 (s, 1H), 7.15 (m, 5H), 12.6 (s, 1H).

To a solution of oxime (850 mg, 3.3 mM) in dichloromethane (15 mL) was added octyl isocyanate (1.6 mL, 10 mM). The resulting solution was stirred overnight. Then the solvent was removed under vacuum to give a yellow solid. The crude product was purified by column chromatography (silica gel, petroleum etherethyl acetate) to afford a white solid (1.4 g, 100%); m.p. 67°–68° C.; MS (FAB): 415 (MH+), 285 (100); Analysis calc'd for $C_{24}H_{34}N_2O_4$: C, 69.54; H, 8.27%; Found: C, 69.66; H, 8.27%. $^1$H NMR (CDCl$_3$, 400 MHz): δ0.88 (t, J=6.4 Hz, 3H), 1.30 (m, 8H), 1.36 (s, 6H), 1.60 (t, J=6.0 Hz, 2H), 2.92 (t, J=7.2 Hz, 2H), 3.32 t, J=7.2 Hz, 2H), 3.32 (q, J=6.8 Hz, 2H), 5.84 (s, 1H), 6.18 (t, J=5.6 Hz, 1H), 6.18 (t, J=5.6 Hz, 1H), 7.18 (m, 2H), 7.25 (m, 2H).

EXAMPLE 12

2,2-Dimethyl-4-bromo-5-[[[[(dodecylamino)carbonyl]oxy]imino]phenylmethyl]3(2H)-furanone To a solution of oxime (2 g, 8.65 mM) in carbon tetrachloride (40 ml) and tetrahydrofuran (10 mL) at 0° C. was added N-bromoacetamide (1.35 g, 0.5 mM) in small portions. The reaction was allowed to stir for 1.5 hours at room temperature. Then, the solution was washed with 0.5N aqueous sodium sulfite (2×10 mL) and saturated aqueous sodium chloride (10 ml). The resulting extract was dried over MgSO$_4$, filtered and concentrated under vacuum to give a yellow solid (2.62 g, 92% ) $^1$H NMR (CDCl$_3$, 200 MHz): δ1.48 (s, 6H), 7.48 (s, 5H).

To a solution of bromo oxime (2.62 g, 8.45 mM) in pyridine (3 ml) was added DMAP (262 mg) and dodecyl isocyanate (4 ml, 16.9 mM). The reaction was allowed to stir overnight. The reaction was diluted with ethyl acetate (200 ml). The resulting organic layer was washed with 1N aqueous hydrochloric acid (2×30 ml) and saturated aqueous sodium chloride (30 ml). The organic layer was then dried over MgSO$_4$, filtered and concentrated under vacuum to give a red semisolid. The crude product was purified by column chromatography (silica gel, dichloromethane-ethyl acetate) to afford an off-white solid (3.42 g, 76%). An analytically pure sample was made by trituration with petroleum ether-ether (10:1); m.p. 61.5°–62.5° C. $^1$H NMR (CDCl$_3$, 400 MHz): δ0.88 (t, J=6.6 Hz, 6H), 1.30 (m, 18 Hz), 1.48 (s, 6H), 1.59 (t, J=5.5 Hz, 1H), 3.34 (dr, $J_1$=6.8 Hz, $J_2$=5.5 Hz, 2H), 6.48 (t, J=5.5 Hz, 1H), 7.44 (m, 5H); MS (CI): 521 (MH+), 186 (100); Analysis calc'd for $C_{26}H_{37}BrN_2O_4$: C, 59.88; H, 7.15%; Found C, 59.87; H, 7.13%.

EXAMPLE 13

2,2-Dimethyl-5-[(4-chlorophenyl)[[(dodecylamino)carbonyl]imino]methyl]-2(3H)-furanone To a suspension of sodium hydride (60%, 13.4 g, 335 mM) in dry DMSO (200 ml) was added a solution of furanone (20 ml, 160 mM) and 1-fluoro-4-nitrobenzene (16.8 ml, 160 mM) in DMSO (200 ml) dropwise. After addition, reaction was stirred 1 hour. Because starting material was observed in TLC, more sodium hydride (2 g, 50 mM) was added. After the mixture was stirred for 15 minutes, the reaction solution was slowly quenched by addition to a mixture of 1N aqueous hydrochloric acid (350 ml) and ice (200 ml). The resulting solution was extracted with ether (6×100 ml). The combined ethereal extracts were washed with water (2×100 ml), dried over MgSO$_4$, filtered and concentrated under vacuum to a dark oil. The crude product was purified by column chromatography (silica gel, dichloromethane-ethyl acetate) to afford an orange solid (20.6 g, 52.4%). 1H NMR (CDCl$_3$, 200 MHz): δ1.37 (s, 6H), 3.88 (s, 2H), 5.33 (s, 1H), 7.42 (d, J=8 Hz, 2H), 8.2 (d, J=8 Hz, 2H).

To a solution of 4-nitrophenyl furanone (10.2 g, 41.3 mM) in concentrated aqueous hydrochloric acid (150 ml) at 0° C. was added stannous chloride hydrate (29 g, 128 mM) in small portions. The reaction was allowed to stir for 3 hours at room temperature. The reaction was not complete by TLC analysis. More stannous chloride hydrate (5.8 g, 25.6 mM) was added and the reaction was stirred overnight. Then, the mixture was slowly added to a mixture of concentrated aqueous ammonium hydroxide (150 ml) and ice (200 g). Then 50% aqueous sodium hydroxide was added till all the precipitate dissolved. The resulting solution was extracted with dichloromethane (5×100 ml). The combined organic extracts were dried over $MgSO_4$, filtered and concentrated under vacuum to yield a brown solid (7.3 g, 81%). $^1$H NMR ($CDCl_3$, 200 MHz): δ1.38 (s, 6H), 3.66 (s, 2H), 5.27 (s, 1H), 6.65 (d, J=8 Hz, 2H), 7.05 (d, J=8 Hz, 2H).

To a solution of 4-aminophenyl furanone (1.0 g, 4.6 mM) and copper chloride (0.74 g, 5.5 mM) in acetonitrile (50 ml) was added isoamyl nitrite (0.93 ml, 6.9 mM). After the reaction was stirred 30 minutes, the solution was added to a mixture of 1N aqueous hydrochloric acid (100 ml) and saturated aqueous sodium chloride (100 ml). The resulting mixture was extracted with ether (3×100 ml). The combined ethereal extracts were dried over $MgSO_4$, filtered and concentrated under vacuum to yield a dark oil. The crude product was purified by column chromatography (silica gel, petroleum ether-ethyl acetate) to afford a yellow liquid (500 mg, 46%). $^1$H NMR ($CDCl_3$, 200 MHz): δ1.39 (s, 6H), 3.78 (s, 2H), 5.30 (s, 1H), 7.23 (m, 5H).

To a solution of 4-chlorophenyl furanone (840 mg, 3.5 mM) in ether (25 ml) was added a 1M ethereal solution of hydrochloric acid (0.5 ml, 25 mM) and isoamyl nitrite (0.54 ml, 3.9 mM). The reaction was allowed to stir overnight. The reaction was concentrated and the residue triturated with petroleum ether (10 ml). The product was filtered and dried to yield a cream colored solid (689 mg, 74%). $^1$H NMR ($CDCl_3$, 200 MHz): 1.35 (s, 6H), 5.72 (s, 1H), 7.36 (d, J=8 Hz, 2H), 7.43 (d, J=8 Hz, 2H).

To a solution of oxime (689 mg, 259 mM) in dry tetrahydrofuran (25 ml) was added dodecyl isocyanate (2.2 ml, 9.8 mM). The resulting solution was stirred for 6 days. Then the reaction was concentrated under vacuum and the residue purified by chromatography (silica gel, petroleum ether-ethyl acetate) to afford a white solid (710 mg, 57%); m.p. 91°–92° C.; MS (CI): 286 (100); Analysis calc'd for: $C_{26}H_{37}O_4N_2Cl$: C, 65.46; H, 7.82%; Found: C, 65.87; H, 8.03%. $^1$H NMR ($CDCl_3$, 400 MHz): δ0.87 (t, J=7 Hz, 3H), 1.29 (br s, 16H), 1.58 (t, J=6.8 Hz, 2H), 3.30 (q, J=6.4 Hz, 2H), 5.70 (s, 1H), 6.11 (J=5.2 Hz, 1H), 7.36 (d, J=8.2 Hz, 2H), 7.45 (d, J=8.4 Hz, 2H).

EXAMPLE 14

Phenyl(2-pyridinyl)methanone O-[(cyclohexylamino)carbonyl]oxime

To a solution of oxime (1.0 g, 5.0 mM) in dichloromethane (20 ml) was added cyclohexyl isocyanate (1.9 ml, 15 mM). The reaction was allowed to stir overnight at room temperature. The reaction was concentrated under vacuum and the residue was triturated with petroleum ether (10 ml). the resulting product was filtered and dried to afford a white solid (1.6 g, 100%); m.p. 130°–131° C.; MS (EI): 181 (100); Analysis calc'd for $C_{19}H_{21}N_3O_2$: C, 70.57; H, 6.55%; Found: C, 70.56; H, 6.59%. $^1$H NMR ($CDCl_3$, 400 MHz): δ1.22 (m, 2H), 1.36 (q, J=9.6 Hz, 2H); 1.63 (br d, J =13.2 Hz, 1H), 1.73 (dd, $J_1$=13.2 Hz, $J_2$=3.6 Hz, 2H), 2.02 (br d, j=9.6 Hz, 2H), 3.66 (m, 1H), 6.09 (d, J=8 Hz, 1H), 7.36 (m, 1H), 7.63 (br s, 5H), 7.79 (m, 2H), 8.65 (d, J=4.8 Hz, 1H).

The compounds of Examples 15 and 16 were prepared by the procedure described in Example 14 with the appropriate isocyanate.

EXAMPLE 15

Phenyl(2-pyridinyl)methanone O-[(octylamino)carbonyl]oxime

Prepared in 98% yield; m.p. 76°–78° C. $^1$H NMR (DMSO-$d_6$, 400 MHz): δ0.84 (t, J=6.7 Hz, 3H), 1.25 (br s, 8H), 1.47 (bt, J=5.6 Hz, 2H), 3.07 (dt, $J_1$=6.8 Hz, $J_2$=6.5 Hz, 2H), 7.32 (m, 2H), 7.47 (m, 4H), 7.66 (t, J=5.6 Hz, 1H), 7.95 (dr, $J_1$=8 Hz, $J_2$=1.8 Hz, 1H), 8.16 (d, J=8 Hz, 1H), 8.54 d, J=4.8 Hz, 1H); MS (EI): 99 (100); Analysis calc'd for $C_{21}H_{27}N_3O_2$: C, 71.36; H, 7.70%; Found: C, 71.41; H, 7.84%.

EXAMPLE 16

Di(2-pyridinyl)methanone O-[(octylamino)carbonyl]oxime

Prepared in 94% yield; m.p. 77°–79° C. $^1$H NMR ($CDCl_3$, 400 MHz): δ(2.86 (t, J=6.8 Hz, 3H), 1.27 (m, 8H), 1.57 (t, J=6.8 Hz, 2H), 3.29 (dt, $J_1$=6.8 Hz, $J_2$=5.2 Hz, 2H), 6.30 (t, J=5.2 Hz, 2H), 7.34 (m, 2H), 7.66 (d, J=8 Hz, 1H), 7.80 (m, 3H), 8.59 (d, J=4.8 Hz, 1H), 8.68 (d, J=4.8 Hz, 1H); MS (EI): 355 (MH+), 200 (100); Analysis calc'd for $C_{20}H_{26}O_4N_2$: C, 67.77; H, 7.39%; Found C, 67.56; H, 7.39%.

EXAMPLE 17

(4-Fluorophenyl)(2-pyridinyl)methanone O-[(octylamino)carbonyl]oxime

To a solution of 2-pyridinecarboxaldehyde (5 ml, 525 mM) in ether (200 ml) at 0° C. was added dropwise a 2.0M ethereal solution of 4-fluorophenylmagnesium bromide (31.5 ml, 63 mM). After the reaction was allowed to stir 3 hours at room temperature, pH 7 phosphate buffer (100 ml) was added and the mixture stirred 30 minutes. The resulting mixture was extracted with ether (3×200 ml). The combined ethereal layers were dried over $MgSO_4$, filtered and concentrated under reduced pressure to yield a yellow solid (10.9 g, ~100%). The crude product was dissolved in dichloromethane (250 ml). To this solution, pyridinium chlorochromate (17 g, 78.8 mM) was added in small portions. After the reaction was stirred for 2.5 hours, ether (500 ml) was added and the mixture was vigorously stirred for 30 minutes. The resulting mixture was filtered through a silica gel plug. The plug was washed with ether till no product was observed in TLC. The filtrate was concentrated under reduced pressure to give a yellow solid (5.4 g, 49%). $^1$H NMR ($CDCl_3$, 200 MHz): δ7.15 (t, J=8 Hz, 2H), 7.48 (m, 1H), 7.88 (t, J=4 Hz, 1H), 8.04 (m, 3H), 8.74 (d, J=4 Hz, 1H).

To a solution of ketone (5.4 g, 26.9 mM) and hydroxylamine hydrochloride (5.6 g, 80.6 mM) in ethanol (90 ml) and water (90 ml) at 0° C. was added dropwise a 50% aqueous solution of sodium hydroxide (7.2 g, 90 mM). The reaction was allowed to stir at room temperature overnight. Then, the reaction was diluted with ethyl acetate (50 ml) and the layers separated. The organic layer was washed with saturated aqueous sodium chloride (2×60 ml), dried over $MgSO_4$, filtered and concentrated under vacuum to give a yellow solid. The crude product was purified by column chromatography (silica gel, hexane-ethyl acetate) to afford a white crystalline solid (3.8 g, 65%, 33.5% from starting aldehyde). $^1$H NMR (CDCl$_3$, 200 MHz): δ7.25 (m, 5H), 7.85 (m, 2H), 8.42 (d, J=6 Hz, 1H), 11.7 (s, 1H).

To a solution of oxime ( 1.0 g, 4.6 mM) in dichloromethane (20 ml) was added octyl isocyanate (2.3 ml, 13,8 mM). The resulting solution was allowed to stir 3 days. After the reaction was concentrated under reduced pressure, the residue was triturated twice with hexane (50 ml). The product was filtered and dried to afford a white solid (1.0 g, 59%); m.p. 72°-74° C. $^1$H NMR (CDCl$_3$, 400 MHz): δ0.88 (t, J=6.8 Hz, 3H), 1.28 (m, 8H), 1.59 (, J=6.8 Hz, 2H), 3.32 (q, J=7 Hz, 2H), 6.29 (t, J=5.2 Hz, 1H), 7.14 (t, J=8 Hz, 2H), 7.39 (t, J=6 Hz, 1H), 7.46 (m, 2H), 7.81 (m, 1H), 8.66 (d, J=3.2 Hz, 1H); MS (EI): 372 (MH+), 217 (100); Analysis calc'd for C$_{21}$H$_{26}$N$_3$O$_2$F: C, 67.9; H, 7.06%; C, 7.94; H, 7.11%.

The compounds in Examples 18 through 21 were prepared by the procedure described in Example 17 using the appropriate organometallic reagent and 2-cyano or carboxaldehyde pyridine.

EXAMPLE 18

(4-Methoxyphenyl)(2-pyridinyl)methanone O-[(octylamino)carbonyl]oxime

Prepared in 91% yield from oxime; m.p. 97°-100° C. MS (FAB): 384 (MH+), 211 (100); Analysis calc'd for C$_{22}$H$_{29}$N$_3$O$_2$: C, 68.90; H, 7.62%; Found: C, 68.61; H, 7.56%. $^1$H NMR (CDCl$_3$, 400 MHz): δ0.87 (t, J=7.2 Hz, 3H), 1.30 (m, 8H), 1.58 (t, J=7.2 Hz, 2H), 3.30 (m, 2H), 3.84 (s, 3H), 6.40 (m, 1H), 6.94 (dd, J$_1$=8 Hz, J$_2$=2 Hz, 2H), 7.37 (m, 1H), 7.44 (dd, J$_1$=9 Hz, J$_2$=2.4 Hz, 2H), 7.75 (m, 2H), 8.66 (d, J$_1$=4.8 Hz, J$_2$=1 Hz, 1H).

EXAMPLE 19

(2-Pyridinyl)(2-thienyl)methanone O-[(butyl amino)carbonyl]oxime

Prepared in 93% from the oxime; m.p. 75°-77° C. $^1$H NMR (CDCl$_3$, 400 MHz): δ0.97 (t, J=6.4 Hz, 3H), 1.38 (dr, J$_1$=15 Hz, J$_2$=7.4 Hz, 2H) 1.58 (m, 2H), 3.34 (q, J=7.3 Hz, 2H), 6.34 (s, 1H), 7.11 (q, J=4 Hz, 1H), 7.47 (m, 2H), 7.69 (m, 2H), 7.85 (dt, J$_1$=10 Hz, J$_2$=1.6 Hz, 1H), 8.74 (d, J=4.5 Hz, 1H); MS (FAB): 304(MH+), 187 (100); Analysis calc'd for C$_{15}$H$_{17}$N$_3$O$_2$S: C, 59.39; H, 5.65%; Found: C, 59.03; H, 5.59%.

EXAMPLE 20

(4-Dimethylamino)phenyl](2-pyridinyl)methanone O-[(butylamino)carbonyl]oxime

Prepared in 47.4% yield form the oxime; m.p. 83°-85° C. $^1$H NMR (CDCl$_3$, 400 MHz): δ0.94 (t, J=7.4 Hz, 3H), 1.38 (m, 2H), 1.57 (m, 2H), 3.00 (s, 6H), 6.46 (t, J=5.5 Hz, 1H), 6.67 (d, J=8 Hz, 1H), 7.36 (m, 1H), 7.46 (d, J=8 Hz, 2H), 7.67 (d, J=8 Hz, 1H), 7.88 (m, 1H), 8.68 (t, J=4 Hz, 1H); MS (FAB): 341 (MH+), 224 (100; Analysis calc'd for C$_{19}$H$_{24}$N$_4$O$_2$: C, 67.04; H, 7.11%; Found: C, 66.56; H, 6.97%.

EXAMPLE 21

(1-Naphthalenyl)(2-pyridinyl)methanone O-[(octylamino)carbonyl]oxime

Prepared in 91% yield form the oxime; m.p. 96°-98° C. $^1$H NMR (CDCl$_3$, 400 MHz): δ0.86 (t, J=6.8 Hz, 3H), 1.26 (m, 8H), 1.54 (m, 2H), 3.25 (q, J=7.2 Hz, 2H), 6.09 (t, J=6 Hz, 1H), 7.31 (m, 1H), 7.39 (dt, J$_1$=8 Hz, J$_2$=1 Hz, 2H), 7.47 (dt, J$_1$=1.2 Hz, J$_2$=8 Hz, 2H), 8.59 (d, J=4.8 Hz, 1H); MS (FAB): 404 (MH+), 231 (100); Analysis calc'd for C$_{25}$H$_{29}$N$_3$O$_2$: C, 74.41; H, 7.24%; Found: C, 74.06; H, 7.35%.

EXAMPLE 22

5H-Indene[1,2-b]pyridin-5-one O-[(octylamino)carbonyl]oxime

A mixture of 5H-indeno[1,2-b]pyridin-5-one (3.5 g, 20.8 mM), hydroxylamine hydrochloride (4.3 g, 62.4 mM) and 50% aqueous sodium hydroxide (4.9 g, 62.4 mM) in ethanol was stirred three days. The solution was concentrated under vacuum and the residue triturated with water. The product was filtered and dried to give a yellow powder (3.8 g, 93%); m.p. 245°-247° C.; Analysis calc'd for C$_{12}$H$_8$N$_2$O: C, 73.46; H, 4.11%; Found: C, 73.24; H, 4.22%.

The above oxime was converted to compound 22 by the procedure used in Example 14. Prepared in 51% yield; m.p. 75°-78° C. $^1$H NMR (CDCl$_3$, 400 MHz): δ0.89 (t, J=6.4 Hz, 3H), 1.34 (m, 8H), 1.65 (quintuplet, J=7.2 Hz, 2H), 3.41 (quartet, J=6.8 Hz, 2H), 6.59 (t, J=5.2 Hz, 1H), 7.22 (m, 1H), 7.51 (m, 2H), 8.59 (m, 1H); MS (FAB): 352 (MH+), 197 (100); Analysis calc'd for C$_{21}$H$_{25}$N$_3$O$_2$: C, 71.77; H, 7.17%; Found: C, 71.51; H, 7.29%.

EXAMPLE 23

5H-Indeno[1,2-b]pyridine-5-one O-[(4-methyl-1-piperidinyl)carbonyl]oxime

The previous oxime was converted to compound 23 by the procedure used in Example 3. Prepared in 30% yield, m.p. 128°-130° C. $^1$H NMR (CDCl$_3$, 400 MHz): δ0.99 (d, J=6.6 Hz, 3H), 1.26 (m, 2H), 1.58 (m, 1H), 1.75 (br d, J=13.2 Hz, 2H), 2.95 (m, 1H), 3.08 (m, 1H), 7.23 (dd, J$_1$=7.7 Hz, J$_2$=5.1 Hz, 1H), 7.42 (t, J=7.6 Hz, 1H), 7.51 (t, J=7.6 Hz, 1H), 7.91 (d, J=7.6 Hz, 1H), 8.02 (d, J=7.6 Hz, 1H), 8.32 (d, J=6.6 Hz, 2H), 8.60 (d, J=6.6 Hz, 1H); MS (EI): 321 (M+), 126 (100); Analysis calc'd for C$_{19}$H$_{19}$N$_3$O$_2$: C, 71.01; H. 5.96%; Found: C, 70.92; H, 5.90%.

EXAMPLE 24

9H-Xanthen-9-one O-[(butylamino)carbonyl]oxime

A solution of ketone (9.8 g, 50 mM) and Lawesson's reagent (10.1 g, 25 mM) in benzene (50 ml) was heated at reflux overnight. After reaction was cooled to room temperature, the mixture was filtered through a silica gel pad. After the pad was washed with dichloromethane (100 mL), the filtrate was concentrated under vacuum to yield a green solid. The crude product was purified by chromatography (silica gel, benzene then dichloromethane) to afford a yellow solid (10.6 g, ~100%). A solution of thioketone (10.6 g, 50 mM) and hydroxylamine hydrochloride (10.6 g, 162.8) in pyridine (100 mL) was heated at reflux overnight. The reaction was slowly added to water (500 ml) after cooling to room temperature. The ensuing precipitate was filtered and dried under vacuum to yield a tan solid (9.2 g, 81% from ketone); m.p. 165°-167° C.; MS (EI): 211 (M+).

A solution of oxime (1.05 g, 5 mM), DMAP (62 mg, 0.5 mM) and butyl isocyanate (1.1 ml, 10 mM) in chloroform (25 ml) was stirred overnight. The precipitate was filtered and triturated in ether (20 ml) overnight. The product was filtered and dried to give an off white solid (1.2 g, 77%); m.p. 118°–119° C. 1H NMR (DMSO-d6, 400 MHz): δ0.90 (t, J=7.3 Hz, 3H), 1.32 (m, 2H), 1.51 (m, 2H), 3.17 (q, J=7.2 Hz, 2H), 7.35 (m, 3H), 7.46 (dd, $J_1=8$ Hz, $J_2=1$ Hz, 6.8 Hz, $J_2=1.6$ Hz, 1H), 7.69 (dt, $J_1=6.8$ Hz, $J_2=1.6$ Hz, 1H), 7.85 (t, J=5.8 Hz, 1H), 8.33 (dd, $J_1=8$ Hz, $J_2=1.4$ Hz, 1H), 8.87 (dd, $J_1=8$ Hz, $J_2=1.4$ Hz, 1H); MS(EI): 310 (M+), 211 (100); Analysis calc'd for $C_{18}H_{18}N_2O_3$: C, 68.66; H, 5.85%; Found: C, 69.48; H, 5.88%.

EXAMPLE 25

9H-Thiaxanthen-9-one O-[(butylamino)carbonyl]oxime 10,10-dioxide

A solution of thioketone (3 g, 13.16 mM) and 30% aqueous hydrogen peroxide (10 ml) in glacial acetic acid (50 ml) was heated at reflux overnight. After reaction was cooled to room temperature, the precipitate was filtered and product was washed with cold glacial acetic acid (10 ml). The product was dried under vacuum to give a yellow crystalline solid (2.38 g, 70%); m.p. 184°–185° C.

A solution of sulfone ketone (2.38 g, 9.15 mM) and hydroxylamine hydrochloride (2.4 g, 40 mM) in pyridine (30 ml) was heated at reflux overnight. After the reaction was cooled to room temperature, the solution was poured into water (100 ml). The resulting aqueous solution was extracted with ethyl acetate (3×200 ml). The organic extracts were dried over MgSO4, filtered and concentrated to a tan solid. The crude product was purified by chromatography (silica gel, chloroform) to afford a yellow solid (2.0 g, 84%); m.p. 219°–220° C.

A solution of oxime (1.95 g, 7.53 mM) DMAP (80 mg, 0.75 mM) and butyl isocyanate (1.7 ml, 15 mM) in chloroform (40 ml) was stirred at room temperature one day. After solution was concentrated under vacuum, the residue was purified by column chromatography (silica gel, petroleum ether-ethyl acetate) and trituration with ether to yield a white solid (2.2 g, 82%); m.p. 111°–112° C. 1H NMR (DMSO-d6, 400 MHz): δ0.88 (t, J=7.2 Hz, 3H), 1.31 (m, 2H), 1.48 (m, 2H), 3.13 (q, J=6 Hz, 2H), 7.85 (m, 4H), 7.93 (t, J=6 Hz, 1H), 8.10 (m, 2H), 8.19 (dd, $J_1=7.8$ Hz, $J_2=1.6$ Hz, 1H), 8.35 (dd, $J_1=7.8$ Hz, $J_2=1.6$ Hz, 1H); MS(EI): 359 (MH+), 260 (100; Analysis calc'd for $C_{18}H_{18}N_2O_4S$: C, 60.32; H, 5.06%; Found: C, 60.29; H, 4.97%.

The compounds of this invention are inhibitors of cholesterol ester hydrolase. It has been shown that removal of the enzyme from pancreatic juice results in 80% reduction in the uptake of cholesterol into the bloodstream in rats [J. Biol. Chem., 262; 260 (1987)]. The association between high cholesterol levels and coronary heart disease is well documented; consequently, compounds with such a profile maybe useful for treating atherosclerosis, familial hypercholesterolemia, hyperlipaemia, and, like diseases. The in vitro and in vivo biological results are presented in Table I. The in vivo assay is given below.

Assay:
Cholesterol absorption was measured in normal rats following simultaneous oral doses of the test compounds and radioactive cholesterol according to the method of Cayen and Dvornik except that [4-14C] cholesterol in propylene glycol and olive oil (vehicle for test compound) were used. Serum radioactivity was measured at 6 hr (Cayen, M. N. and Dvornik D., J. Lipid Res., 20, 162 (1979).

| Ex. | IC$_{50}$ (μM) against CEH | % Decrease (mg/kg) $^{14}$C Chol. Absorption at 6 hr in normal rat |
| --- | --- | --- |
| 1 | 1.9 | 39 (100) |
| 2 | 0.57 | 76 (100) |
| 3 | 0.1 | 44 (100) |
| 4 | 5.4 | 74 (100 |
| 5 | 25 | 39 (25) |
| 6 | 2.7 | 50 (25) |
| 7 | 1.9 | 47 (100) |
| 8 | 0.13 | 46 (100) |
| 9 | 2.64 | 62 (100) |
| 10 | 12.7 | 46 (100) |
| 11 | 1.5 | 57 (100) |
| 12 | 2.27 | 69 (100) |
| 13 | 10 | 63 (100) |
| 14 | 1.4 | 44 (100) |
| 15 | 2.31 | 78 (100) |
| 16 | 2.77 | 39 (50) |
| 17 | 0.44 | 57 (50) |
| 18 | 2.1 | 45 (65) |
| 19 | 0.47 | 71 (65) |
| 20 | 4.6 | 51 (65) |
| 21 | 5.3 | 53 (100) |
| 22 | 0.62 | 54 (50) |
| 23 | 0.03 | 44 (50) |
| 24 | 0.6 | 54 (50) |
| 25 | 0.13 | 34 (50) |

We claim:
1. The compounds of formula (I)

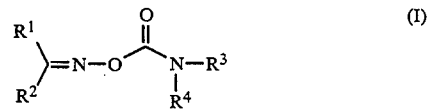

wherein $R^1$ and $R^2$ are independently phenyl, thienyl, naphthyl, substituted phenyl wherein the substituent is selected from the group consisting of halogen, methoxy, and dialkylamino wherein alkyl contains 1 to 3 carbon atoms; or $R^1$ and $R^2$ are independently substituted furanone of the structure

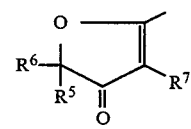

wherein $R^5$ and $R^6$ are independently alkyl containing 1 to 3 carbon atoms, cycloalkyl containing 5 to 7 carbon atoms, phenyl or substituted phenyl wherein the substituent is alkyl containing 1 to 5 carbon atoms or halogen; $R^7$ is hydrogen or halogen; or
$R^1$ and $R^2$ are joined to form

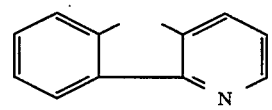

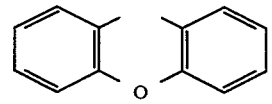

or

-continued

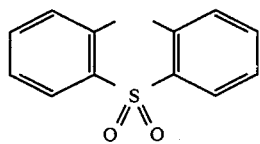

R³ and R⁴ are independently hydrogen, hydrocarbyl containing 4 to 20 branched, straight chain, cyclic, saturated or unsaturated carbon atoms; or
R³ and R⁴ are joined to form

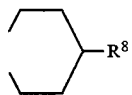

wherein R⁸ is alkyl containing 1 to 3 carbon atoms.

2. The compounds according to claim 1 of formula (II)

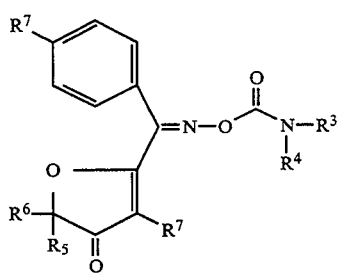

wherein R⁵ and R⁶ are independently alkyl containing 1 to 3 carbon atoms, cycloalkyl containing 5 to 7 carbon atoms, phenyl or substituted phenyl wherein the substituent is alkyl containing 1 to 5 carbon atoms or halogen; R⁷ is hydrogen or halogen;
R³ and R⁴ are independently alkyl containing 4 to 20 branched, straight chain, cyclic, saturated or unsaturated carbon atoms.

3. The compounds according to claim 2 designated 2,2-dimethyl-5-[[[[(octylamino)carbonyl]oxy]imino]-phenylmethyl]-3(2H)-furanone;
2,2-dimethyl-5-[[[[(dodecylamino)carbonyl]oxy]imino]phenylmethyl]-3(2H)-furanone;
2,2-dimethyl-5-[[[[[(4,4dimethylcyclohexyl)amino]-carbonyl]oxy]imino]phenylmethyl]-3(2H)-furanone;
2,2-dimethyl-5-[[[[[(2)-9-octadecenylamino]carbonyl]oxy]imino]phenylmethyl]-3(2H)-furanone;
2,2-dimethyl-5-[[[[[(E)-10-nonadecenylamino]carbonyl]oxy]imino]phenylmethyl]-3(2H)-furanone;
2,2-dimethyl-5-[[[[[(E,E)-9,12-octadecadienylamino]-carbonyl]oxy]imino]phenylmethyl]-3(2H)-furanone; 2-cyclohexyl-2-methyl-5-[[[[(octylamino)carbonyl]oxy]imino]phenylmethyl]-3(2H)-furanone
2-methyl-2-phenyl-5-[[[[(octylamino)carbonyl]oxy]imino]phenylmethyl]-3(2H)-furanone; 2-(4-chlorophenyl)-2-methyl-5-[[[[(octylamino)carbonyl]oxy]imino]phenylmethyl]-3(2H)-furanone;
2-[4-(1,1-dimethylethyl)phenyl]-2-methyl-5-[[[[(octylamino)carbonyl]oxy]imino]phenylmethyl]-3(2H)-furanone;
2,2-dimethyl-4-bromo-5-[[[[(dodecylamino)carbonyl]imino]phenylmethyl]-3(2H)-furanone; and
2,2-dimethyl-5-[(4-chlorophenyl)[[(dodecylamino)-carbonyl]imino]methyl]-2(3H)-furanone.

4. The compounds according to claim 1 designated 5H-indeno[1,2-b]pyridin-5-one O-[(octylamino)carbonyl]oxime;
5H-indeno[1,2-b]pyridine-5-one O-[(4-methyl-1-piperidinyl)carbonyl]oxime;
9H-xanthen-9-one O-[(butylamino)carbonyl]oxime; and
9H-thiaxanthen-9-one O-[(butylamino)carbonyl]oxime 10,10-dioxide.

5. A pharmaceutical composition, which comprises an alleviating amount of a compound of claim 1 and a pharmaceutically acceptable carrier.

6. A method for lowering blood cholesterol which comprises administering to a patient in need of lowered cholesterol, an effective amount of a compound of claim 1.

* * * * *